United States Patent [19]

Kruck et al.

[11] Patent Number: 5,073,645
[45] Date of Patent: Dec. 17, 1991

[54] CVD-COMPATIBLE TUNGSTEN HALOGEN PHOSPHINE COMPLEX COMPOUNDS AND METHODS FOR THE PRODUCTION THEREOF

[75] Inventors: Thomas Kruck, Erfstadt; Norbert Behrendorf, Cologne; Heiko Faubel, Huerth, all of Fed. Rep. of Germany

[73] Assignee: Siemens Aktiengesellschaft, Munich, Fed. Rep. of Germany

[21] Appl. No.: 370,040

[22] Filed: Jun. 22, 1989

[30] Foreign Application Priority Data

Aug. 18, 1988 [DE] Fed. Rep. of Germany ....... 3828125

[51] Int. Cl.⁵ .............................................. C07F 11/00
[52] U.S. Cl. .......................................... 556/13; 556/1; 556/26; 423/53; 423/60
[58] Field of Search ................. 556/1, 13, 26; 423/53, 423/59, 60

[56] References Cited

U.S. PATENT DOCUMENTS 3,619,288  11/1971  Sirtl ..................................... 117/227
3,661,843  5/1972  Hechenbleikner et al. ...... 556/13 X
4,012,399  3/1977  Hechenbleikner et al. .......... 556/13

FOREIGN PATENT DOCUMENTS 1900119  1/1969  Fed. Rep. of Germany .

OTHER PUBLICATIONS

Article by T. H. Kruck et al, from the periodical "Anorganische Allgemeine Chemie", 397, 1973, pp. 31–39.
Article by T. H. Kruck et al, from the periodical "Angewandte Chemie", 79, 1967, pp. 27–43.
Photoelectron Spectroscopic Study of Metal Trifluorophosphine and Hydridotrifluorophosphine Complexes, Journal of the Chemical Society Dalton Transactions 20, 1975, pp. 2054–2059.
Synthesis, Mass Spectra, Raman and Infrared Spectra of the Complexes M (PF$_3$)$_6$ (M=Cr. Mo, W), Journal of Organometallic Chemistry 57, 1973, pp. 169–181.
Trifluorophosphine Complexes of Transition Metals, Angewandte Chemie International Edition, vol. 6, No. 1, 1967, pp. 53–67.

*Primary Examiner*—Arthur G. Prescott
*Attorney, Agent, or Firm*—Hill, Van Santen, Steadman & Simpson

[57] ABSTRACT

The present invention is directed to tungsten halogen phosphine complex compounds having the formula $W(PX_3)_{6-n}L_n$ wherein X is fluorine or chlorine, L is molecular nitrogen, acetone or other ketones or aldehydes, carbon monoxide, acetonitrile or other nitriles, diphenylethine or other ethines, diethylether or tetrahydrofurane or other open-chained or cyclic ethers, benzene or other aromatics, ethene or 1,5-cyclooctodiene or cycloheptatriene or other mono, di, or, respectively, triolefines, whereby two single-tooth ligands L can be replaced by one $\mu^4$-ligand or three single-tooth ligands L can be replaced by one $\mu^6$-ligand and n is a whole number from 0 to 5, as well as methods for the manufacture thereof. These substances are easily volatile in a vacuum and can be decomposed at extremely low temperatures and are therefore extremely well suited for CVD depositions in semiconductor technology, particularly, as via hole fillers in VLSI circuits.

10 Claims, No Drawings

CVD-COMPATIBLE TUNGSTEN HALOGEN PHOSPHINE COMPLEX COMPOUNDS AND METHODS FOR THE PRODUCTION THEREOF

BACKGROUND OF THE INVENTION

The present invention relates to CVD-compatible tungsten halogen phosphine complex compounds and methods of synthesizing same.

In recent years, the areas of metallo-organic and coordination chemistry have experienced incredible growth due to the increasing technological importance of these fields. Examples of the broad spectrum in which metallo-organic species are utilized include the frequent application of organic synthesis, the stabilization of reactive particles such as, for example, arines, carbenes, alkines by metallic coordination, and homogeneous catalysis via intermediate organo-metal stages. A more recent utilization of compounds of this species is the use of metal deposition, from these compounds, utilizing CVD-methods (chemical vapor deposition). To accomplish such a deposition, metal complexes that are readily volatile and thermically decomposable are necessary.

An article by Th. Kruck in the periodical "Angewandte Chemie" 79 (1967), pages 27–43, discloses the purification of an inorganic ligand trifluorophosphine. It has been found that an acceptor capability at the ligand $PF_3$ is present in this compound that is greater than that of the previously known transition metal carbonyls.

From another article by Th. Kruck et al, in the periodical "Anorganische Allgemeine Chemie" 397 (1973), pages 31-39, a compound, hexakis (trifluorophosphine) tungs (0) having the chemical formula $W(PF_3)_6$ can be derived. Utilizing a method of "reductive trifluorophosphination" results in a 42% yield of the compound.

German Published Application No. 1 900 119 also discloses the use of metal trifluorophosphines. Metal layers, that are used as contact metal layers in semiconductor technology, are deposited on substrates by a thermic decomposition of metal (0) complexes, known at that time and their hydride derivatives, at temperatures from 350°-600° C. and reduced pressure.

SUMMARY OF THE INVENTION

The present invention provides new compounds of tungsten with halogen phosphine ligands without, or, respectively, with additional ligands that can be used for metallization in semiconductor technology. The compounds are especially adapted to be utilized as via hole fillers in VLSI circuits. Methods of synthesis of the compounds are also provided.

To this end, CVD-compatible tungsten halogen phosphine complex compounds are provided having the formula $$W(PX_3)_{6-n}L_n$$

wherein: L is molecular nitrogen ($N_2$), acetone (($CH_3)_2CO$) or other ketones or aldehydes, carbon monoxide (CO), acetonitrile $CH_3CN$) or other nitriles, diphenylethine ($C_6H_5C\equiv CC_6H_5$) or other ethines, diethyether ($Et_2O$) or tetrahydrofurane (THF) or other open-chained or cyclic ethers, benzene ($C_6H_6$) or other aromatics, ethene ($C_2H_4$) or 1,5-cyclooctadiene (COD) or cycloheptatriene (CHT) or other mono, di, or, respectively, triolefins, whereby two single-tooth ligands L ("single-tooth" refers to a molecule that provides only one electron pair for a donor/acceptor complex and can therefore occupy only one coordination location at a corresponding acceptor) can be replaced by one $\mu^4$-ligand or three-tooth ligands L can be replaced by one $\mu^6$-ligand; and n is a whole number from 0 to 5.

In an embodiment, X is not fluorine [and] when n is 0.

In an embodiment, X is chlorine and n is 0.

In an embodiment, X is fluorine, n is 1, and L is nitrogen ($N_2$).

In an embodiment, X is fluorine, n is 1, and L is acetone (($CH_3)_2CO$).

In an embodiment, X is fluorine, n is 1, and L is carbon monoxide (CO).

In an embodiment, X is fluorine, n is 2, and $L_2$ is 1,5-cyclooctadiene, norbornadiene, or other dienes.

In an embodiment, X is fluorine, n is 3, and $L_3$ is a $\mu^6$-arene such as benzene, toluene, or 1,3,5-trimethylbenzene.

In an embodiment, X is fluorine, n is 3, and $L_3$ is a $\mu^6$-triene such as cycloheptatriene.

In an embodiment, a method for producing hexakis (trifluorophosphine) tungsten having the formula $W(PF_3)_6$ is provided wherein tungsten hexacarbonyl is photochemically converted with trifluorophosphine.

In an embodiment, a method for producing hexakis (trifluorophosphine) tungsten having the formula $W(PF_3)_6$ is provided wherein anionic $[W(PF_3)_5X]-$ complexes, having X as a halide, are converted under pressure with copper powder and trifluorophosphine. In a further embodiment, tungsten sulfide ($WS_2$) is used instead of $[W(PF_3)_5X]-$.

In an embodiment, a method for producing hexakis (trifluorophosphine) tungsten having the formula $W(PF_3)_6$ is provided wherein $[W(PF_3)_5X]-$ complexes are converted with a Lewis acid in the presence of trifluorophosphine.

In an embodiment, a method for producing hexakis (trifluorophosphine) tungsten having the formula $W(PF_3)_6$ is provided wherein tungsten halides are reduced by magnesium anthracene under $PF_3$ pressure.

In an embodiment, a method for producing derivatives of hexakis (trifluorophosphine) tungsten having the formula $W(PF_3)_{6-n}L_n$, wherein n 32 1 to 5, is provided, wherein hexakis (trifluorophosphine) tungsten is photochemically converted with the appertaining ligand.

In an embodiment, a method for producing derivatives of hexakis (trifluorophosphine) tungsten having the formula $W(PF_3)_{6-n}L_n$, wherein n=1 to 5, is provided, wherein a tungsten trifluorophosphine complex having the formula $W(PF_3)_{6-n}L_n$ is converted thermically and/or under pressure with other ligands L' to form a $W(PF_3)_{6-n}L_n$ complex.

In an embodiment, a method for producing derivatives of hexakis (trifluorophosphine) tungsten having the formula $W(PF_3)_{6-n}L_n$, wherein n=1 to 5 is provided, wherein a tungsten carbonyl complex having the formula $W(CO)_{6-n}L_n$, wherein n=0 to 4, is photochemically converted with trifluorophosphine Additional features and advantages of the present invention are described in, and will be apparent from, the detailed description of the presently preferred embodiments.

DETAILED DESCRIPTION OF THE PRESENTLY PREFERRED EMBODIMENTS

The present invention provides new compound types, from coordination chemistry of tungsten (O) with halogen phosphine ligands ($PF_3$ or, respectively, $PCl_3$) without or, respectively, with additional ligands (L). The compounds are suitable for use as metallizations in semiconductor technology, particularly as via hole fillers in VLSI circuits. The present invention also provides methods for the synthesis thereof. It is important that these compounds decompose at optimally low temperatures.

To this end, the present invention provides tungsten halogen phosphine complex compounds having the formula:

$$W(PX_3)_{6-n}L_n$$

wherein:

X is fluorine or chlorine; and

L is molecular nitrogen ($N_2$), acetone (($CH_3)_2CO$) or other ketones or aldehydes, carbonmonoxide (CO), acetonitrile ($CH_3CN$) or other nitriles, diphenylethine ($C_6H_5C\equiv CC_6H_5$) or other ethines, diethylether ($Et_2O$) or tetrahydrofurane (THF) or other open-chained or cyclic ethers, benzene ($C_6H_6$) or other aromatics, ethene ($C_2H_4$) or 1,5-cyclooctadiene (COD) or cycloheptatriene (CHT) or other mono, di, or, respectively, triolefines, whereby two single-tooth ligands L can be replaced by one $\mu^4$-ligand or three single-tooth ligands L can be replaced by $\mu^6$-ligand and n is a whole number from 0 to 5.

The above compounds, because they are easily volatization in a vacuum, and due to their easy thermal decomposition at very low temperatures (some of the compounds decompose at between 50° to about 100° C.) these compounds are especially suited for use as a homogeneous filling for via holes etched in insulating layers with tungsten, as required in the manufacture of VLSI memory circuits. In this regard, they can be used both for thermic chemical vapor deposition (CVD) as well as for plasma-induced CVD. Further, the use of laser CVD is also possible.

By way of example, and not limitation, examples of the present invention will be set forth. In the examples set forth below, examples 1 to 3 disclose the preparation of hexakis (trifluorophosphine) tungsten, $W(PF_3)_6$, and examples 4 to 8 disclose the preparation of $W(PF_3)_6$ derivatives having the formula $W(PF_3)_{6-n}L_n$, wherein n=1 to 5. The latter are frequently distinguished by a high volatility in a vacuum and by low chemical and thermic stability relative to $W(PF_3)_6$.

First Exemplary Embodiment

In an inside irradiation apparatus, 2 grams of $W(CO)_6$ were dissolved in 260 milliliters of pentane and 10 milliliters of 1,3,5-trimethylbenzene. The composition was cooled to −50° C. After saturation with $PF_3$, irradiation with a Hg high-pressure burner was performed for five days, during which re-saturation with $PF_3$ was repeatedly performed. The solvent was then withdrawn at room temperature and the product was crystallized out of the remaining 1,3,5-trimethylbenzene at −30° C. and was sublimated at 40° C./$10^{-2}$ mbar. Pursuant to the procedure, 0.5 grams of colorless crystals were obtained.

Second Exemplary Embodiment

In a rotating autoclave filled with 6 grams $PPN[W(PF_3)_5Cl]$ (PPN representing bis(triphenylphosphine) nitrogenium), a sufficient amount of $PF_3$ was condensed in at −196° C. to obtain a pressure of 200 bar at room temperature. The autoclave was rotated at 150° C. for three to four days in a heatable agitator stand. After the reaction time was completed, the resultant content was introduced into a Schlenk pipe cooled to −196° C. The excess $PF_3$ was slowly condensed out. The residue was sublimated at 50° C. in a high vacuum.

Third Exemplary Embodiment 5 grams of $PPN[W(PF_3)_5Cl]$ was dissolved in 100 milliliters of ether. The mixture was cooled to −50° C. and saturated with $PF_3$ and then laced portion-by-portion with 1 gram of $AlCl_3$. The solvent was then withdrawn. The resultant product was then sublimated at 50° C./$10^{-2}$ mbar. Pursuant to the procedure, 1 gram of colorless crystals was obtained.

Fourth Exemplary Embodiment

In this example, the complex $W(PF_3)_5N_2$ was produced.

To this end, in an outside irradiation apparatus, 0.6 grams of $W(PF_3)_6$ was dissolved in 120 milliliters of freshly distilled ether (without stabilizer) and the solution was cooled to −15° C. Irradiation was then performed for two hours while passing a weak nitrogen stream therethrough. Upon retention of the nitrogen stream, agitation was performed for another hour at −15° C. and the solution was slowly brought to room temperature. The solvent was then withdrawn in a vacuum. A yellow-brown oil was then dissolved in pentane and filtered. The product obtained after the removal of the solvent was cleaned by being dissolved twice in 10 milliliters of pentane and then precipitated at −78° C. The crystals formed in this manner were sublimated at 50° C./$10^{-3}$ mbar. Pursuant to this method, 240 milligrams of light yellow crystals were obtained.

Fifth Exemplary Embodiment

In this example, the complex $W(PF_3)_5(CH_3)_2CO$ was produced.

0.5 grams of $W(PF_3)_6$ was dissolved in 120 milliliters ether and irradiated for two hours in a crystal outside irradiation apparatus at −15° C. This resulted in the creation of the solvent complex $W(PF_3)_5Et_2O$. One milliliter of acetone was then subsequently added and this was thawed to room temperature. After agitation overnight, the solvent was withdrawn and the product was sublimated at 30° C./$10^{-2}$ mbar. Pursuant to this method, 200 milligrams of yellow crystals were obtained.

Sixth Exemplary Embodiment

In this example, the complex $W(PF_3)_5CO$ was produced.

To this end, in a glass inside irradiator 2 grams of $W(CO)_6$ was dissolved in 260 milliliters of pentane and ten milliliters of 1,3,5-trimethylbenzene; the mixture was then cooled to −50° C. After saturation with $PF_3$, irradiation was performed for five days, whereby resaturation with $PF_3$ was repeatedly performed. After a withdrawal of the solvent, the product was crystallized out of the remaining 1,3,5-trimethylbenzene at −30° C. and was sublimated at 20° C./$10^{-2}$ mbar. The procedure resulted in the production of 0.5 grams of colorless crystals.

Seventh Exemplary Embodiment

In this example, the complex $W(PF_3)_4(\mu^4\text{-}L)$ wherein L represents 1,5-cyclooctadiene (COD), was produced.

In a crystal outside irradiation apparatus, 0.7 grams of $W(PF_3)_6$ was dissolved in 80 milliliters of pentane and 20 milliliters of COD and irradiated for one hour at $-5°$ C. After the solvent was withdrawn at room temperature and the COD distilled off at $50°$ C./$10^{-2}$ Torr, the product was sublimated at $80°/10^{-2}$ mbar. The procedure resulted in the production of 150 milligrams of yellow crystals.

Eighth Exemplary Embodiment

In this example, the complex $W(PF_3)_3\ (\mu^6\text{-}L)$, wherein L represents benzene ($C_6H_6$), was produced.

In a crystal outside irradiation apparatus, 0.4 grams of $W(PF_3)_6$ was dissolved in 100 milliliters of benzene and 20 milliliters of pentane and the mixture was irradiated for 30 minutes at $0°$ C. The solvent was then withdrawn and the benzene distilled off in a high vacuum. The product was then sublimated at $80°$ C./$10^{-2}$ mbar. Pursuant to the procedure, 120 milligrams of yellow crystals were obtained.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A chemical vapor deposition-compatible tungsten halogen phosphine complex compound having the formula:

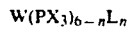

$$W(PX_3)_{6-n}L_n$$

wherein:
X is chosen from the group consisting of fluorine and chlorine; and
L is chosen from the group consisting of molecular nitrogen ($N_2$), acetone (($CH_3)_2CO$) and other ketones and aldehydes, carbon monoxide (CO), acetonitrile ($CH_3CN$) and other nitriles, diphenylethine ($C_6H_5{\equiv}CC_6H_5$) and other ethines, diethylether ($Et_2O$), tetrahydrofurane (THF) and other open-chained or cyclic ethers, benzene ($C_6H_6$) and other aromatics ethene ($C_2H_4$), 1, 5-cyclooctadiene (COD), cycloheptatriene (CHT) and other mono, di, and triolefins, whereby two single-tooth ligands L will be replaced by one $\mu^4$-ligand or three-tooth ligands L will be replaced by one $\mu^6$-ligands and n is a whole number from 0 to 5 and wherein when n is 0 X is not fluorine.

2. The tungsten halogen phosphine compound of claim 1 wherein X is chlorine and n is 0.

3. The tungsten halogen phosphine compound of claim 1 wherein X is fluorine, n is 1, and L is nitrogen ($N_2$).

4. The tungsten halogen phosphine compound of claim 1 wherein X is fluorine, n is 1, and L is acetone (($CH_3)_2CO$).

5. The tungsten halogen phosphine compound of claim 1 wherein X is fluorine, n is 1, and L is carbon monoxide (CO).

6. The tungsten halogen phosphine compound of claim 1 wherein X is fluorine, n is 2, and $L_2$ is chosen from the group consisting of 1,5-cyclooctadiene, norbornadiene, and other dienes.

7. The tungsten halogen phosphine compound of claim 1 wherein x is fluorine, n is 3, and $L_3$ is $\mu^6$-arene.

8. The tungsten halogen phosphine compound of claim 7 wherein $L_3$ is chosen from the group consisting of benzene, toluol, and 1,3,5-trimethylbenzene.

9. The tungsten halogen phosphine compound of claim 1 wherein X is fluorine, n is 3, and $L_3$ is $\mu^6$-triene.

10. The tungsten halogen phosphine compound of claim 1 wherein $L_3$ is cycloheptatriene.

* * * * *